United States Patent
Ohta et al.

(10) Patent No.: US 9,268,041 B2
(45) Date of Patent: Feb. 23, 2016

(54) RADIOGRAPHIC IMAGE DETECTION DEVICE, RADIOGRAPHIC IMAGE DETECTION METHOD, AND COMPUTER-READABLE STORAGE MEDIUM

(75) Inventors: Yasunori Ohta, Kanagawa (JP); Naoyuki Nishino, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 398 days.

(21) Appl. No.: 13/594,303

(22) Filed: Aug. 24, 2012

(65) Prior Publication Data
US 2013/0083892 A1  Apr. 4, 2013

(30) Foreign Application Priority Data

Sep. 30, 2011 (JP) ................................ 2011-218045

(51) Int. Cl.
G01T 1/17 (2006.01)
G01N 23/04 (2006.01)
G01T 1/20 (2006.01)
A61B 6/00 (2006.01)

(52) U.S. Cl.
CPC .............. *G01T 1/2018* (2013.01); *A61B 6/548* (2013.01); *G01T 1/17* (2013.01)

(58) Field of Classification Search
CPC .... A61B 6/4233; A61B 6/4283; A61B 6/548; H04N 5/378; G01T 1/247; G01T 1/17; G01T 1/2018
USPC ............ 378/62, 98.8, 19; 250/370.08, 370.09
See application file for complete search history.

(56) References Cited

U.S. PATENT DOCUMENTS

| 4,595,949 A | 6/1986 | Fenster et al. |
| 4,670,893 A * | 6/1987 | Tsuchiya ...................... 378/105 |
| 5,090,040 A * | 2/1992 | Lanza et al. .................... 378/62 |
| 5,142,286 A * | 8/1992 | Ribner et al. ................. 341/143 |
| 7,268,715 B2 * | 9/2007 | Guimaraes .................... 341/143 |

(Continued)

FOREIGN PATENT DOCUMENTS

| JP | 7-36614 | 4/1995 |
| JP | 2005-94108 | 4/2005 |

(Continued)

OTHER PUBLICATIONS

Japanese Office Action dated Aug. 5, 2014, in corresponding Japanese Patent Application No. 2011-218045.

*Primary Examiner* — Wyatt Stoffa
(74) *Attorney, Agent, or Firm* — Young & Thompson

(57) ABSTRACT

A radiographic image detection device includes: an image pickup unit with plural radiation detection portions arrayed in a two-dimensional form and detect radiation, and that captures a radiographic image; a radiographic image generating unit having plural analog signal generating units that generate analog signals corresponding to radiation doses; a conversion unit that converts the generated analog signals into digital signals; a judging unit that judges whether or not level fluctuations of the generated analog signals are within a predetermined threshold value; and a control unit that controls the conversion unit such that an analog signal, at which it is judged that the level fluctuation is within the predetermined threshold value, is converted into a digital signal, and that controls the conversion unit such that an analog signal, at which it is judged that the level fluctuation has exceeded the predetermined threshold value, is not converted into a digital signal.

20 Claims, 9 Drawing Sheets

(56) References Cited

U.S. PATENT DOCUMENTS

| | | | |
|---|---|---|---|
| 7,573,037 B1 * | 8/2009 | Kameshima et al. | 250/370.09 |
| 7,768,002 B2 | 8/2010 | Kitamura et al. | |
| 7,795,590 B2 | 9/2010 | Takahashi et al. | |
| 7,964,849 B2 | 6/2011 | Takahashi et al. | |
| 8,148,695 B2 | 4/2012 | Takahashi et al. | |
| 8,565,358 B2 * | 10/2013 | Komaili et al. | 375/345 |
| 2002/0012450 A1 * | 1/2002 | Tsujii | 382/103 |
| 2003/0038942 A1 * | 2/2003 | Hameister et al. | 356/446 |
| 2008/0259177 A1 * | 10/2008 | Oike | 348/222.1 |
| 2009/0026379 A1 | 1/2009 | Yaegashi et al. | |
| 2009/0033532 A1 * | 2/2009 | Reshef et al. | 341/137 |
| 2009/0185642 A1 * | 7/2009 | Razzell | 375/340 |
| 2009/0224235 A1 | 9/2009 | Kitamura et al. | |
| 2009/0290680 A1 * | 11/2009 | Tumer et al. | 378/62 |
| 2010/0215146 A1 * | 8/2010 | Rao et al. | 378/62 |
| 2011/0215254 A1 * | 9/2011 | Takahashi et al. | 250/394 |
| 2012/0114099 A1 * | 5/2012 | Yoshida | 378/62 |
| 2012/0211662 A1 * | 8/2012 | Shimizukawa et al. | 250/369 |
| 2013/0026263 A1 * | 1/2013 | Bamber et al. | 241/24.1 |
| 2013/0208860 A1 * | 8/2013 | Sugizaki | 378/62 |
| 2014/0018027 A1 * | 1/2014 | Wilhelmsson et al. | 455/234.1 |

FOREIGN PATENT DOCUMENTS

| | | | |
|---|---|---|---|
| JP | 2006-247102 | | 9/2006 |
| JP | 2008-107326 | | 5/2008 |
| JP | 2008-177735 | | 7/2008 |
| JP | 2008177735 A | * | 7/2008 |
| JP | 2009-032854 | | 2/2009 |
| JP | 2009-212389 | | 9/2009 |
| JP | 2010-127903 | | 6/2010 |
| JP | 2011-004857 | | 1/2011 |

* cited by examiner

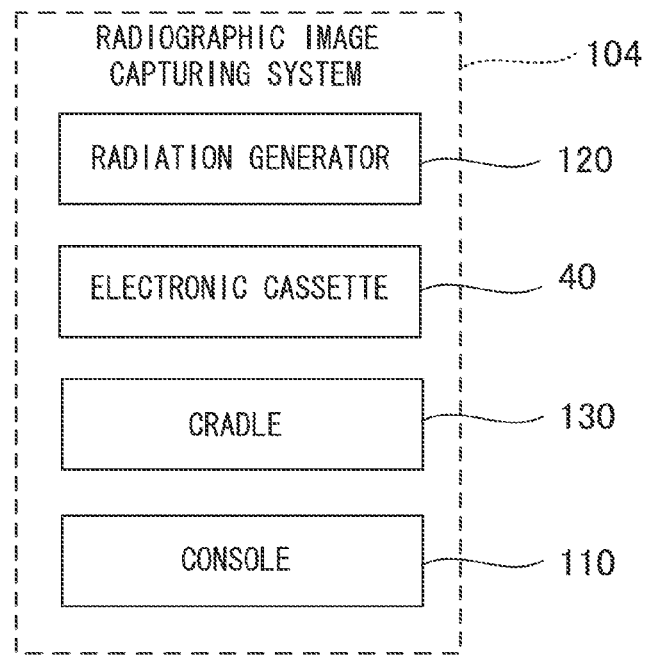
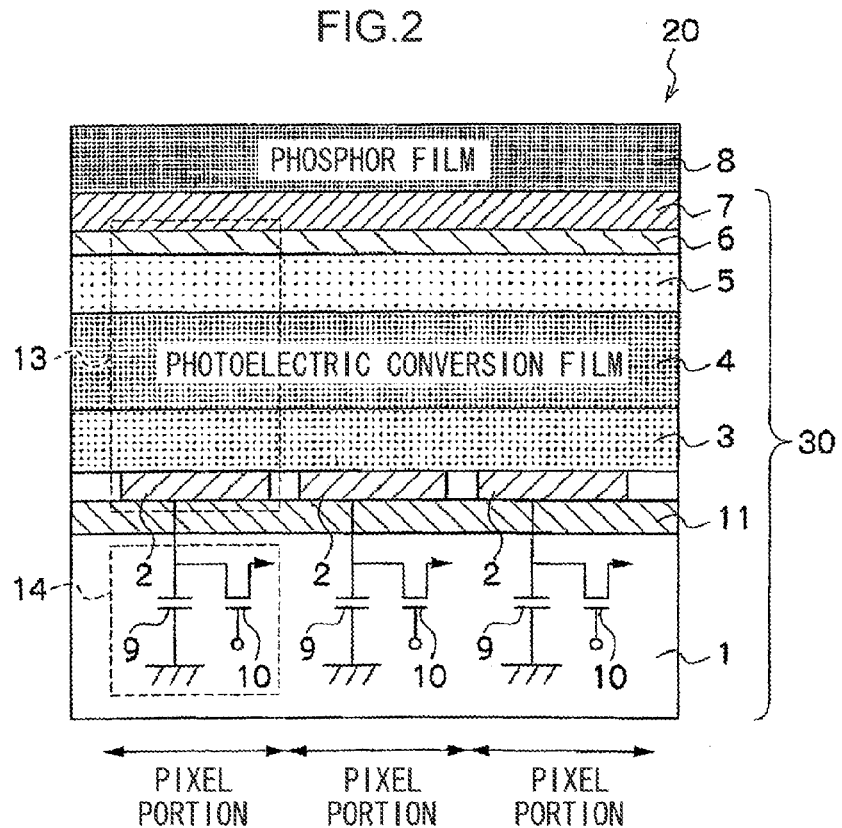

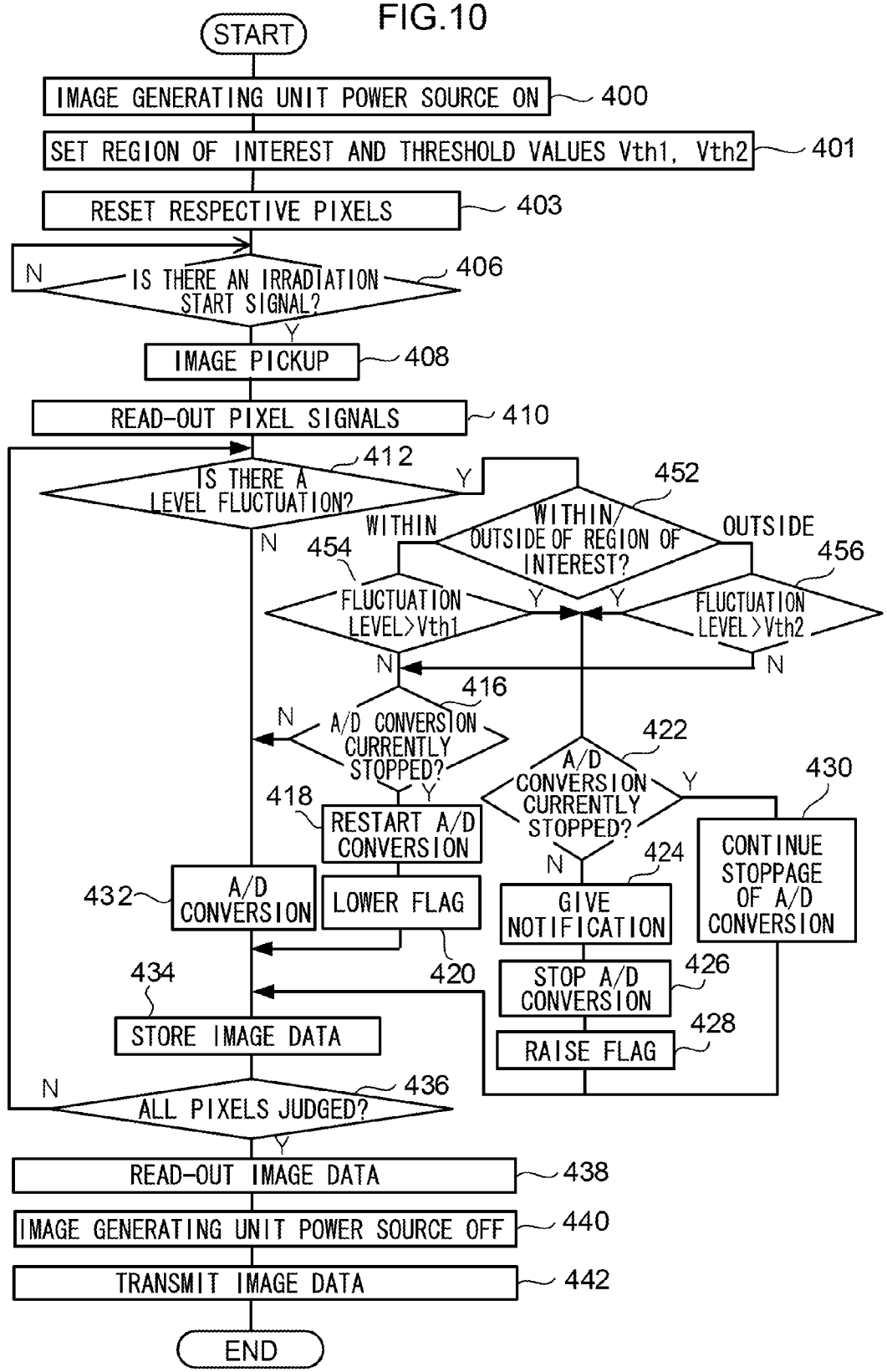

RADIOGRAPHIC IMAGE DETECTION DEVICE, RADIOGRAPHIC IMAGE DETECTION METHOD, AND COMPUTER-READABLE STORAGE MEDIUM

CROSS-REFERENCE TO RELATED APPLICATION

This application is based on and claims priority under 35 USC 119 from Japanese Patent Application No. 2011-218045 filed on Sep. 30, 2011, which is incorporated by reference herein.

BACKGROUND

1. Technical Field

The present invention relates to a radiographic image detection device, a radiographic image detection method and a computer-readable storage medium, and in particular, relates to a radiographic image detection device such as a radiographic image detection panel or the like, and a radiographic image detection method and a computer-readable storage medium.

2. Related Art

Radiation detectors such as FPDs (Flat Panel Detectors), in which a radiation-sensitive layer is disposed on a TFT (Thin Film Transistor) active matrix substrate and that detect irradiated radiation such as X-rays or the like and output electric signals expressing the radiographic image expressed by the detected radiation, and the like have been put into practice in recent years. As compared with a conventional imaging plate, this radiation detector has the advantages that images can be confirmed immediately, and video images also can be confirmed. Further, portable radiographic image capturing devices (hereinafter also called electronic cassettes), that incorporate such a radiation detector therein and store radiographic image data outputted from the radiation detector, also are being put into practice. Because the electronic cassette has excellent portability, images of a patient can be captured while the patient lies as is on a stretcher or a bed, and it is also easy to adjust the region to be imaged by changing the position of the electronic cassette. Therefore, even cases in which images of a patient who cannot move are to be captured can be dealt with flexibly.

On the other hand, in an electronic cassette that handles weak signals such as radiographic image signals, there is the possibility that external noise or the like will affect the radiation detector. If noise becomes mixed-in with the radiographic image signals, it is difficult to acquire high-quality radiographic images. For example, Japanese Patent Application Laid-Open (JP-A) No. 2006-247102 discloses the following technique in an imaging device that usually carries out communication with a control device: unintended artifacts arise in acquired images due to the effects of power source voltage/ground potential fluctuations from the communication module that is usually operating, or due to the effects of radiation noise that accompanies the communication operation, and therefore, at the time of reading-out the acquired image charges of the imaging device, the communication module within the imaging unit is stopped so as to enable acquisition of good images.

Further, JP-A No. 2011-4857 discloses the following technique: in elongated imaging that carries out imaging at plural imaging regions by moving the irradiated region of radiation and a radiographic image generating device (an FPD), unintended image noise arises in the radiographic image data at times of reading-out the image data and at times of communicating. Therefore, in the elongated imaging, by not carrying out the radiographic image data read-out operation during movement of the imaging region, good radiographic image data is acquired.

However, stopping the communication module at times of reading-out acquired image charges of the imaging device, or not carrying out the radiographic image data read-out operation during movement of the imaging region, as in the techniques disclosed in aforementioned JP-A No. 2006-247102 and JP-A No. 2011-4857, limits the stopping of the read-out operation of the imaging device and the read-out capability of the imaging device. As a result, there is the problem that the user operability for the technician who is capturing the radiographic images and for the subject (the patient) is poor, such as preparations for the next imaging cannot be carried out, or, even if it is desired to confirm an image immediately after the image capturing, the captured image cannot be displayed right away, or the like.

SUMMARY

The present invention was made in consideration of the above-described problem, and an object thereof is to provide a radiographic image detection device in which needless operation stoppage time does not arise in the image pickup work or the image pickup processing even if a noise source is driven.

A radiographic image detection device relating to a first aspect of the present invention has: an image pickup unit that has plural radiation detection portions that are arrayed in a two-dimensional form and detect radiation, and that captures a radiographic image expressed by radiation that has been transmitted through an object of imaging and been incident on the image pickup unit; a radiographic image generating unit having plural analog signal generating units that are provided in respective correspondence with the plural radiation detection portions and that each generate an analog signal corresponding to a radiation dose detected at the corresponding radiation detection portion; a conversion unit that converts the analog signals, that are generated respectively at the plural analog signal generating units, into digital signals; a judging unit that judges whether or not a level fluctuation of the analog signal generated at each of the plural analog signal generating units is within a predetermined threshold value; and a control unit that controls the conversion unit such that an analog signal, at which it is judged by the judging unit that the level fluctuation is within the predetermined threshold value, is converted into a digital signal, and that controls the conversion unit such that an analog signal, at which it is judged that the level fluctuation has exceeded the predetermined threshold value, is not converted into a digital signal.

In accordance with a radiographic image detection device relating to a second aspect, each of the plural analog signal generating units includes an amplifier that generates an analog signal by amplifying a signal corresponding to a radiation dose detected at the radiation detection portion.

In accordance with a radiographic image detection device relating to a third aspect, the control unit effects control so as to add identification data, that expresses a time when the level fluctuation of the analog signal exceeded the threshold value, to digital image data that is expressed by a digital signal obtained by conversion at the conversion unit, and so as to store the digital image data in a storage unit.

In accordance with a radiographic image detection device relating to a fourth aspect, the judging unit judges whether or not a level fluctuation of the analog signal is within the predetermined threshold value, at least one of a time of pickup of the radiographic image and a time of standby after irradiation of radiation.

A radiographic image detection device relating to a fifth aspect further has a notification unit that gives notice that the level fluctuation has exceeded the threshold value. Moreover, a radiographic image detection device relating to a sixth aspect further has a stopping unit that stops a radiation source of the radiation when notice is given by the notification unit.

A radiographic image detection device relating to a seventh aspect further has a region designation unit that designates in advance a region of interest in the radiographic image, wherein the threshold value is changed for a level fluctuation of an analog signal that expresses a radiographic image within the region of interest, and for a level fluctuation of an analog signal that expresses a radiographic image outside of the region of interest.

In accordance with a radiographic image detection device relating to an eighth aspect, when a level fluctuation of the analog signal exceeds the threshold value, conversion by the conversion unit of an analog signal that expresses a radiographic image within the region of interest is carried out after a predetermined time elapses from a time when the level fluctuation exceeds the threshold value.

In accordance with a radiographic image detection device relating to a ninth aspect, when a level fluctuation of the analog signal exceeds the threshold value, conversion by the conversion unit of an analog signal that expresses a radiographic image within the region of interest is carried out later than conversion by the conversion unit of an analog signal that expresses a radiographic image outside of the region of interest.

In accordance with a radiographic image detection device relating to a tenth aspect, when the radiographic image is a video image, the threshold value is made to be smaller than when the radiographic image is a still image.

A radiographic image capturing system relating to an eleventh aspect of the present invention has: the above-described radiographic image detection device; a radiation generator; and a console that carries out transmission and reception of data with the radiographic image detection device and the radiation generator.

A radiographic image detection method relating to a twelfth aspect of the present invention includes: by an image pickup unit that has plural radiation detection portions that are arrayed in a two-dimensional form and detect radiation, capturing a radiographic image expressed by radiation that has been transmitted through an object of imaging and been incident on the image pickup unit; by each of plural analog signal generating units that are provided in respective correspondence with the plural radiation detection portions, generating an analog signal that corresponds to a radiation dose detected at the corresponding radiation detection portion; judging whether or not a level fluctuation of the analog signal generated at each of the plural analog signal generating units is within a predetermined threshold value; and carrying out conversion into a digital signal on an analog signal, at which it is judged that the level fluctuation is within the predetermined threshold value, and stopping conversion into a digital signal of an analog signal, at which it is judged that the level fluctuation has exceeded the predetermined threshold value.

A computer-readable storage medium relating to a thirteenth aspect of the present invention is a computer readable storage medium that stores a program for causing execution of processing by a radiographic image detection device that has: an image pickup unit that has plural radiation detection portions that are arrayed in a two-dimensional form and detect radiation, and that captures a radiographic image expressed by radiation that has been transmitted through an object of imaging and been incident on the image pickup unit; a radiographic image generating unit having plural analog signal generating units that are provided in respective correspondence with the plural radiation detection portions and that each generate an analog signal corresponding to a radiation dose detected at the corresponding radiation detection portion; and a conversion unit that converts the analog signals, that are generated respectively at the plural analog signal generating units, into digital signals, the processing including: judging whether or not a level fluctuation of the analog signal generated at each of the plural analog signal generating units is within a predetermined threshold value; and controlling the conversion unit such that an analog signal, at which it is judged by the judging unit that the level fluctuation is within the predetermined threshold value, is converted into a digital signal, and controlling the conversion unit such that an analog signal, at which it is judged that the level fluctuation has exceeded the predetermined threshold value, is not converted into a digital signal.

In this way, in accordance with the present invention, there is the excellent effect that, when a level fluctuation is sensed in analog signal output, an image that contains noise is not outputted, and therefore, interpretation is not affected.

BRIEF DESCRIPTION OF THE DRAWINGS

An exemplary embodiment of the present invention will be described in detail based on the following figures, wherein:

FIG. 1 is a drawing showing the schematic structure of a radiographic image capturing system relating to an exemplary embodiment of the present invention;

FIG. 2 is a sectional schematic drawing showing the schematic structure of three pixel portions of a radiation detector relating to the exemplary embodiment;

FIG. 10 is a flowchart showing the order of processings of changing a threshold value of level fluctuation judgment of an amplifier-outputted waveform.

DETAILED DESCRIPTION

Figure 3:
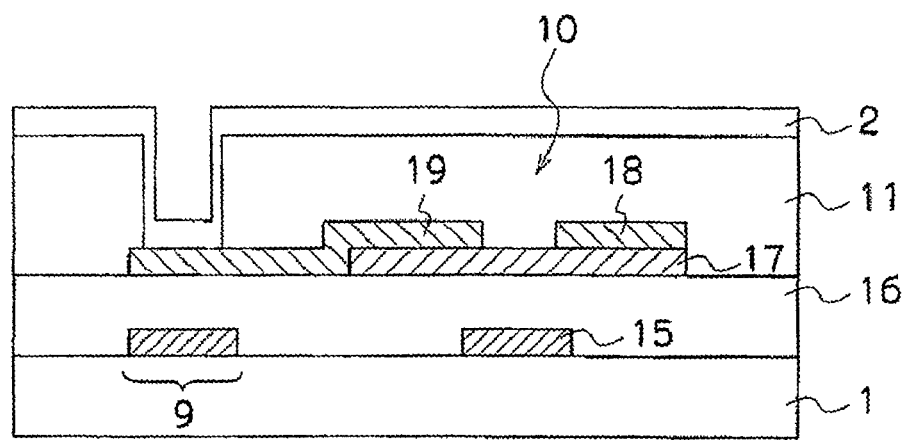
FIG. 3 is a sectional side view schematically showing the structure of a signal output portion of one pixel portion of the radiation detector relating to the exemplary embodiment.

A form for embodying the present invention is described in detail hereinafter with reference to the drawings. FIG. 1 shows the schematic structure of a radiographic image capturing system relating to an exemplary embodiment of the present invention. A radiographic image capturing system 104 shown in FIG. 1 receives an imaging request from an unillustrated terminal device, and, in accordance with instructions from a server that manages the schedule of capturing radiographic images, carries out capturing of radiographic images in accordance with the operation of a doctor or a radiology technician. The radiographic image capturing system 104 has: a radiation generator 120 that irradiates, from a radiation source and onto a subject, radiation X of a dose that is in accordance with exposure conditions; an electronic cassette 40 in which is incorporated a radiation detector 20 that absorbs the radiation X, that has passed through the region that is the object of imaging of the subject, and generates charges, and, on the basis of the generated charge amounts, generates image data that expresses a radiographic image; a cradle 130 that charges a battery incorporated within the electronic cassette 40; and a console 110 that controls the electronic cassette 40 and the radiation generator 120.

In a state in which the electronic cassette 40 is accommodated in an accommodating portion of the cradle 130 at times of non-use, the battery incorporated in the electronic cassette 40 is charged. At times of capturing radiographic images, the electronic cassette 40 is taken-out of the cradle 130 by a radiology technician or the like. When the imaging posture is standing, the electronic cassette 40 is held in the holding portion of a standing stand, and, when the imaging posture is laying-down, the electronic cassette 40 is held in the holding portion of a laying-down stand. At the radiographic image capturing system 104, various types of data are transmitted and received by wireless communication between the radiation generator 120 and the console 110, and between the electronic cassette 40 and the console 110.

Note that the electronic cassette 40 is not used only in a state of being held at the holding portion of a standing stand or the holding portion of a laying-down stand. Owing to the portability thereof, the electronic cassette 40 can be used in a state of not being held at a holding portion, at the time of imaging an arm portion, a leg portion, or the like.

FIG. 2 is a sectional schematic drawing schematically showing the structure of pixel portions of a radiation detector that is incorporated in the electronic cassette of the radiographic image capturing system relating to the exemplary embodiment of the present invention. As shown in FIG. 2, at the radiation detector 20 relating to the present exemplary embodiment, a signal output portion 14, a sensor portion 13 and a scintillator 8 are successively layered on a substrate 1 that is insulating, and a pixel is structured by the signal output portion 14 and the sensor portion 13. Plural pixels are arrayed on the substrate 1, and each pixel is structured such that the signal output portion 14 and the sensor portion 13 overlap at the pixel.

The scintillator 8 is formed on the sensor portion 13 via a transparent insulating film 7, and is formed by deposition of a phosphor that converts radiation, that is incident from the upper side (the side opposite the substrate 1) or the lower side, into light and emits light. By providing this scintillator 8, the scintillator 8 absorbs the radiation, that has passed through the portion that is the object of imaging of the subject, and emits light. The wavelength region of the light that the scintillator 8 emits is preferably the visible light region (wavelengths of 360 nm to 830 nm), and more preferably includes the wavelength region of green color in order to make monochromatic image pickup by the radiation detector 20 possible.

In cases of carrying out image pickup by using X-rays as the radiation, concretely, phosphors that contain cesium iodide (CSI) are preferable as the phosphor that is used at the scintillator 8, and use of CsI(Tl) (cesium iodide to which thallium is added), whose emission spectrum at the time of X-ray irradiation is 400 nm to 700 nm, is particularly preferable. Note that the emission peak wavelength in the visible light region of CsI(Tl) is 565 nm.

The sensor portion 13 has an upper electrode 6, a lower electrode 2, and a photoelectric conversion film 4 that is disposed between these upper and lower electrodes. The photoelectric conversion film 4 is structured from an organic photoelectric conversion material that absorbs the light emitted by the scintillator 8 and generates charges. Because the light generated by the scintillator 8 must be incident on the photoelectric conversion film 4, it is preferable to structure the upper electrode 6 of an electrically-conductive material that is transparent at least with respect to the emission wavelength of the scintillator 8. More concretely, at the upper electrode 6, it is preferable to use a transparent conducting oxide (TCO) whose transmittance with respect to visible light is high and whose resistance value is small. Note that metal thin films of Au or the like can also be used as the upper electrode 6, but, when attempting to obtain transmittance of 90% or greater, it is easy for the resistance value to increase, and therefore, a TCO is more preferable. For example, ITO, IZO, AZO, FTO, $SnO_2$, $TiO_2$, $ZnO_2$ and the like can preferably be used, and ITO is most preferable from the standpoints of simple processing, low resistance, and transparence. Note that the upper electrode 6 may be formed as a single layer that is common to all of the pixels, or may be divided per pixel.

The photoelectric conversion film 4 includes an organic photoelectric conversion material, and absorbs the light emitted from the scintillator 8, and generates charges corresponding to the absorbed light. By utilizing the photoelectric conversion film 4 that contains an organic photoelectric conversion material in this way, there is a sharp absorption spectrum in the visible region, electromagnetic waves other than the light emitted by the scintillator 8 are hardly absorbed at all by the photoelectric conversion film 4, and noise that is generated by radiation such as X-rays or the like being absorbed at the photoelectric conversion film 4 can be suppressed effectively.

In order to most efficiently absorb the light emitted at the scintillator 8, it is preferable that the absorption peak wavelength of the organic photoelectric conversion material that structures the photoelectric conversion film 4 be nearer to the emission peak wavelength of the scintillator 8. Although it is ideal for the absorption peak wavelength of the organic photoelectric conversion material and the emission peak wavelength of the scintillator 8 to coincide, the light emitted from the scintillator 8 can be sufficiently absorbed provided that the difference between the two is small. Concretely, the difference between the absorption peak wavelength of the organic photoelectric conversion material and the emission peak wavelength of the scintillator 8 with respect to radiation is preferably within 10 nm, and more preferably within 5 nm.

Examples of organic photoelectric conversion materials that can satisfy these conditions are quinacridone organic compounds and phthalocyanine organic compounds. For example, because the absorption peak wavelength in the visible region of quinacridone is 560 nm, if quinacridone is used as the organic photoelectric conversion material and CsI(Tl) is used as the material of the scintillator 8, it becomes possible to keep the aforementioned difference in peak wavelengths to within 5 nm, and the charge amount generated at the photoelectric conversion film 4 can be made to be a substantial maximum.

Next, the photoelectric conversion film 4 that can be applied to the radiation detector 20 relating to the present exemplary embodiment is described concretely. The electromagnetic wave absorption/photoelectric conversion region at the radiation detector 20 relating to the present exemplary embodiment can be structured from the pair of electrodes 2, 6, and an organic layer that includes the organic photoelectric conversion film 4 and that is sandwiched between these electrodes 2, 6. More concretely, this organic layer can be formed by layering and superposing, or by mixing together, a region that absorbs electromagnetic waves, a photoelectric conversion region, an electron transport region, a positive hole transport region, an electron blocking region, a positive hole blocking region, a crystallization preventing region, an electrode, an interlayer contact improving region, and the like. This organic layer preferably includes an organic p-type compound or an organic n-type compound.

An organic p-type semiconductor (compound) is a donating organic semiconductor (compound) that is exemplified mainly by positive hole transporting organic compounds, and is an organic compound having the property of easily donating electrons. More specifically, this is the organic compound that has the smaller ionization potential when two organic materials are used by being made to contact one another. Accordingly, any organic compound can be used as the donating organic compound provided that it is an organic compound that has an electronic donating ability.

An organic n-type semiconductor (compound) is an accepting organic semiconductor (compound) that is exemplified mainly by electron transporting organic compounds, and is an organic compound having the property of easily accepting electrons. More specifically, this is the organic compound that has the greater electron affinity when two organic compounds are used by being made to contact one another. Accordingly, any organic compound can be used as the accepting organic compound provided that it is an organic compound that has an electronic accepting ability.

Materials that can be used as the organic p-type semiconductor and the organic n-type semiconductor, and the structure of the photoelectric conversion film 4, are described in detail in JP-A No. 2009-32854, and therefore, description thereof is omitted here. Note that the photoelectric conversion film 4 may be formed so as to further contain fullerene or carbon nanotubes.

Greater film thicknesses of the photoelectric conversion film 4 are preferable from the standpoint of absorbing the light from the scintillator 8. However, if the thickness of the photoelectric conversion film 4 is a certain level or greater, the strength of the electric field generated at the photoelectric conversion film 4 due to the bias voltage applied from the both ends of the photoelectric conversion film 4 decreases, and charges can no longer be collected. Therefore, thicknesses of greater than or equal to 30 nm and less than or equal to 300 nm are preferable, and greater than or equal to 50 nm and less than or equal to 250 nm is more preferable, and greater than or equal to 80 nm and less than or equal to 200 nm is particularly preferable. Note that, in the radiation detector 20 shown in FIG. 2, the photoelectric conversion film 4 is structured as a common single film at all of the pixels, but may be divided per pixel.

The lower electrodes 2 are thin films that are divided per pixel. The lower electrodes 2 can be structured of an electrically-conductive material that is transparent or non-transparent, and aluminum, silver and the like can be suitably used therefor. The thickness of the lower electrodes 2 can be made to be, for example, greater than or equal to 30 nm and less than or equal to 300 nm.

At the sensor portion 13, due to a predetermined bias voltage being applied between the upper electrode 6 and the lower electrode 2, one of the charges (positive holes, electrons) generated at the photoelectric conversion film 4 can be moved to the upper electrode 6, and the other can be moved to the lower electrode 2. At the radiation detector 20, a wire is connected to the upper electrode 6, and bias voltage is applied to the upper electrode 6 via this wire. Further, the polarity of the bias voltage is determined such that the electrons generated at the photoelectric conversion film 4 move to the upper electrode 6 and the positive holes move to the lower electrode 2, but the polarity may be opposite to this.

It suffices for the sensor portion 13 that structures each pixel to include at least the lower electrode 2, the photoelectric conversion film 4 and the upper electrode 6. However, in order to suppress an increase in dark current, it is preferable to provide at least either of an electron blocking film 3 or a positive hole blocking film 5, and it is more preferable to provide both. The electron blocking film 3 can be provided between the lower electrode 2 and the photoelectric conversion film 4, and, when bias voltage is applied between the lower electrode 2 and the upper electrode 6, electrons being injected from the lower electrode 2 into the photoelectric conversion film 4 and dark current increasing can be suppressed. An electron donating organic material can be used for the electron blocking film 3.

It suffices for the material that is used for the electron blocking film 3 in actuality to be selected in accordance with the material of the adjacent electrode and the material of the adjacent photoelectric conversion film 4 and the like. The material that is used for the electron blocking film 3 preferably has a large electron affinity (Ea) of 1.3 eV or more greater than the work factor (Wf) of the material of the adjacent electrode, and has an ionizing potential (Ip) that is equivalent to or less than the Ip of the material of the adjacent photoelectric conversion film 4. Materials that can be applied as the electron donating organic material are described in detail in JP-A No. 2009-32854, and therefore, description thereof is omitted.

In order to reliably exhibit a dark current suppressing effect and to prevent a decrease in the photoelectric conversion efficiency of the sensor portion 13, the thickness of the electron blocking film 3 is preferably greater than or equal to 10 nm and less than or equal to 200 nm, and more preferably greater than or equal to 30 nm and less than or equal to 150 nm, and particularly preferably greater than or equal to 50 nm and less than or equal to 100 nm.

The positive hole blocking film 5 can be provided between the photoelectric conversion film 4 and the upper electrode 6, and, when bias voltage is applied between the lower electrode 2 and the upper electrode 6, can suppress the injection of positive holes from the upper electrode 6 into the photoelectric conversion film 4 and dark current from increasing. An electron receiving organic material can be used for the positive hole blocking film 5. In order to reliably exhibit a dark current suppressing effect and to prevent a decrease in the photoelectric conversion efficiency of the sensor portion 13, the thickness of the positive hole blocking film 5 is preferably greater than or equal to 10 nm and less than or equal to 200 nm, and more preferably greater than or equal to 30 nm and less than or equal to 150 nm, and particularly preferably greater than or equal to 50 nm and less than or equal to 100 nm.

It suffices for the material that is used for the positive hole blocking film 5 in actuality to be selected in accordance with the material of the adjacent electrode and the material of the adjacent photoelectric conversion film 4 and the like. The material that is used for the positive hole blocking film 5 preferably has a large ionizing potential (Ip) of 1.3 eV or more greater than the work factor (Wf) of the material of the adjacent electrode, and has an electron affinity (Ea) that is equivalent to or greater than the Ea of the material of the adjacent photoelectric conversion film 4. Materials that can be applied as the electron receiving organic material are described in detail in JP-A No. 2009-32854, and therefore, description thereof is omitted.

When the bias voltage is set such that, among the charges generated at the photoelectric conversion film 4, the positive holes move to the upper electrode 6 and the electrons move to the lower electrode 2, it suffices for the positions of the electron blocking film 3 and the positive hole blocking film 5 to be opposite. Further, both of the electron blocking film 3 and the positive hole blocking film 5 do not have to be provided, and, if either is provided, a dark current suppressing effect of a certain extent can be obtained.

FIG. 3 schematically shows the structure of the signal output portion that is formed at the surface of the substrate 1 beneath the lower electrode 2 of each pixel. As shown in FIG. 3, a capacitor 9, that accumulates the charges that have moved to the lower electrode 9, and a field-effect thin film transistor (hereinafter also simply called thin film transistor) 10, that converts the charges accumulated at the capacitor 9 into an electric signal and outputs the electric signal, are formed at the signal output portion 14 so as to correspond to the lower electrode 2. The region at which the capacitor 9 and the thin film transistor 10 are formed has a portion that overlaps with the lower electrode 2 in plan view. Due to this structure, there is overlapping, in the thickness direction, between the signal output portion 14 and the sensor portion 13 at each pixel. Note that, in order to make the planar surface area of the radiation detector 20 (the pixels) be a minimum, it is desirable for the region at which the capacitor 9 and the thin film transistor 10 are formed to be completely covered by the lower electrode 2.

The capacitor 9 is electrically connected to the corresponding lower electrode 2 via a wire of an electrically-conductive material that is formed so as to pass through an insulating film 11 that is provided between the substrate 1 and the lower electrodes 2. Due thereto, the charges collected at the lower electrode 2 can be moved to the capacitor 9.

At the thin film transistor 10, a gate electrode 15, a gate insulating film 16 and an active layer (channel layer) 17 are layered, and a source electrode 18 and a drain electrode 19 are formed on the active layer 17 with a predetermined interval therebetween. The active layer 17 can be formed from, for example, amorphous silicon, an amorphous oxide, an organic semiconductor material, carbon nanotubes or the like. Note that the material that structures the active layer 17 is not limited to these.

As amorphous oxides that structure the active layer 17, oxides containing at least one of In, Ga and Zn (e.g., In—O type) are preferable, and oxides containing at least two of In, Ga and Zn (e.g., In—Zn—O type, In—Ga—O type, Ga—Zn—O type) are more preferable, and oxides containing In, Ga and Zn are particularly preferable. As In—Ga—Zn—O type amorphous oxides, amorphous oxides whose composition in a crystalline state is expressed by $InGaO_3(ZnO)_m$ (where m is a natural number of less than 6) are preferable, and in particular, $InGaZnO_4$ is more preferable.

Phthalocyanine compounds, pentacene, vanadyl phthalocyanine, and the like are examples of organic semiconductor materials that can structure the active layer 17, but the organic semiconductor materials are not limited to these. Note that structures of phthalocyanine compounds are described in detail in JP-A No. 2009-212389, and therefore, description thereof is omitted here.

If the active layer 17 of the thin film transistor 10 is formed of an amorphous oxide, an organic semiconductor material, or carbon nanotubes, radiation such as X-rays and the like is not absorbed, or, even if radiation is absorbed, the absorption is limited to an extremely small amount, and therefore, the generation of noise at the signal output portion 14 can be effectively suppressed.

Further, when the active layer 17 is formed of carbon nanotubes, the switching speed of the thin film transistor 10 can be made to be high-speed, and further, the thin film transistor 10 that has a low absorption rate of light in the visible light region can be formed. Note that, when the active layer 17 is formed of carbon nanotubes, the performance of the thin film transistor 10 markedly deteriorates merely due to an extremely small amount of metal impurities being mixed in the active layer 17, and therefore, the active layer 17 must be formed by separating and extracting carbon nanotubes of extremely high purity by centrifugal separation or the like.

Here, with all of the aforementioned amorphous oxides, organic semiconductor materials, and carbon nanotubes that structure the active layer 17 of the thin film transistor 10, and with the organic photoelectric conversion materials that structure the photoelectric conversion film 4, film formation at a low temperature is possible. Accordingly, the substrate 1 is not limited to substrates that are highly heat-resistant such as semiconductor substrates, quartz substrates, glass substrates and the like, and flexible substrates of plastic or the like, and aramid and bio-nanofibers can also be used. Concretely, flexible substrates of polyesters such as polyethylene terephthalate, polybutylene phthalate, polyethylene naphthalate and the like, and polystyrene, polycarbonate, polyethersulfone, polyarylate, polyimide, polycycloolefin, norbornene resins, poly(chlorotrifluoroethylene) and the like can be used. If such a flexible substrate made of plastic is used, lightening of weight can be achieved, which is advantageous in terms of, for example, portability and the like.

Further, an insulating layer for ensuring the insulating ability, a gas barrier layer for preventing passage of moisture and oxygen, an undercoat layer for improving smoothness or a tight fit with the electrodes and the like, or the like may be provided at the substrate 1.

On the other hand, with aramid, high-temperature processes of greater than or equal to 200° can be applied, and therefore, a transparent electrode material can be cured at a high temperature and made to be low resistance. Further, aramid can also be applied to automatic packaging of a driver IC, including the solder reflow process. Moreover, because the thermal expansion coefficient of aramid is close to those of ITO (Indium Tin Oxide) and glass substrates, there is little warping after manufacture, and aramid is difficult to break. Further, aramid can form substrates that are thin as compared with glass substrates or the like. Note that a substrate may be formed by layering an ultra-thin glass substrate and aramid.

Bio-nanofibers are fibers in which a cellulose microfibril bundle (bacteria cellulose) that produces bacteria (acetic acid bacterium, Acetobacter Xylinum), and a transparent resin are compounded. When the cellulose microfibril bundle has a width of 50 nm, the cellulose microfibril bundle is a size of 1/10 with respect to the visible light wavelength, and has high strength, high elasticity, and low thermal expansion. By impregnating and hardening a transparent resin, such as an acrylic resin, an epoxy resin or the like, in bacteria cellulose, bio-nanofibers that exhibit light transmittance of about 90% at a wavelength of 500 nm while containing up to 60 to 70% fiber, are obtained. Bio-nanofibers have a low thermal expansion coefficient (3-7 ppm) that is comparable to that of silicon crystal, have strength (460 MPa) to the same extent as that of steel, have high elasticity (30 GPa), and are flexible. Therefore, the substrate 1 can be formed to be thin as compared with a glass substrate or the like.

In the present exemplary embodiment, a TFT substrate 30 is formed by forming the signal output portions 14, the sensor portions 13 and the transparent insulating film 7 in that order on the substrate 1. The radiation detector 20 is formed by affixing the scintillator 8 onto this TFT substrate 30 by using an adhesive resin or the like having low light absorption.

Figure 4:
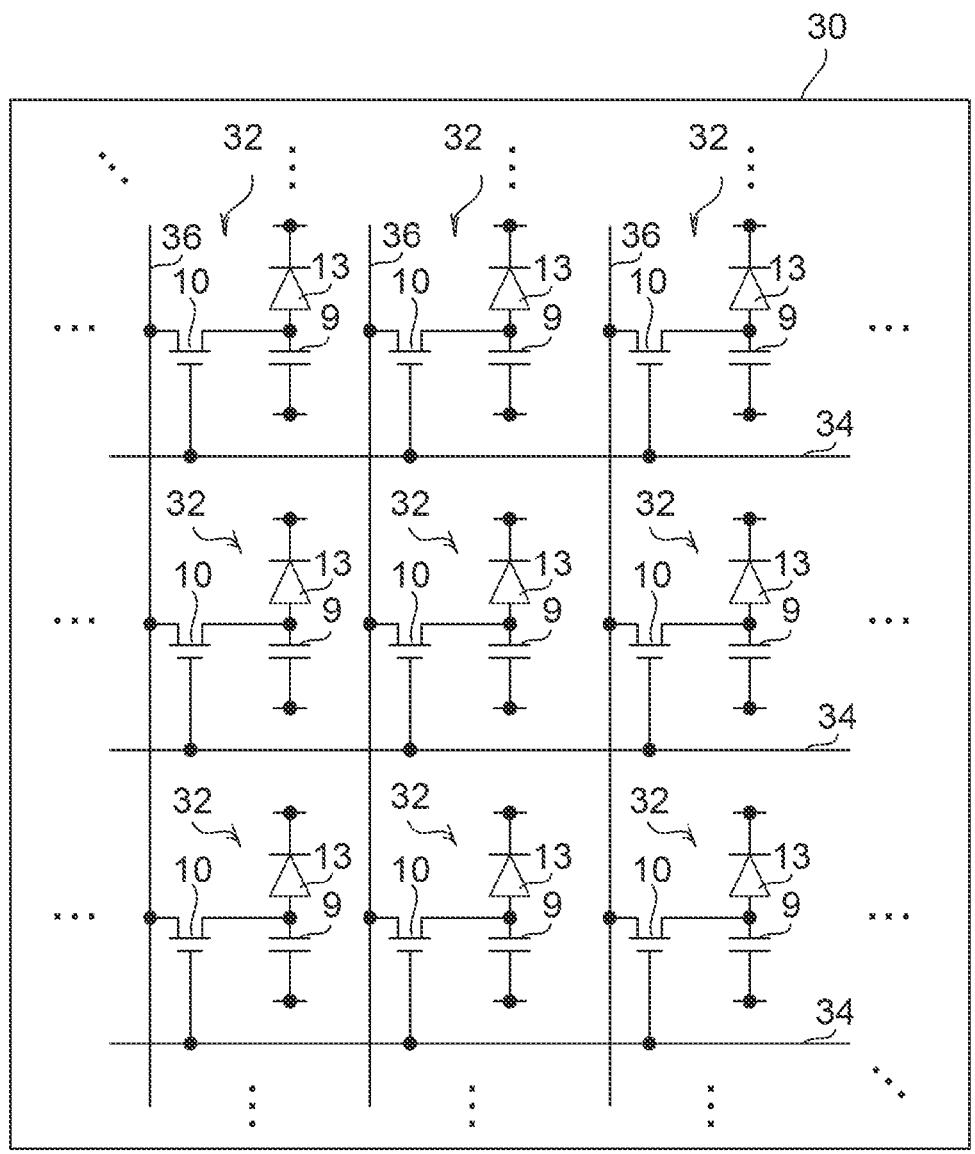
FIG. 4 is a plan view showing the structure of the radiation detector relating to the exemplary embodiment.

FIG. 4 is a plan view showing the structure of the radiation detector of the electronic cassette relating to the present exemplary embodiment. As shown in FIG. 4, plural pixels 32, that are structured to include the above-described sensor portion 13, capacitor 9 and thin film transistor 10, are provided at the TFT substrate 30 in a two-dimensional form in a given direction (the row direction in FIG. 4) and in an intersecting direction (the column direction in FIG. 4) with respect to the given direction.

Further, plural gate lines 34, that extend in the aforementioned given direction (row direction) and are for turning the respective thin film transistors 10 on and off, and plural data lines 36 (signal lines), that extend in the aforementioned intersecting direction (column direction) and are for reading-out charges via the thin film transistors 10 that are in on states, are provided at the radiation detector 20. The radiation detector 20 is formed in a flat plate shape, and, in plan view, in a quadrilateral shape having four sides at the outer edges thereof, and more specifically, a rectangular shape.

Figure 5:
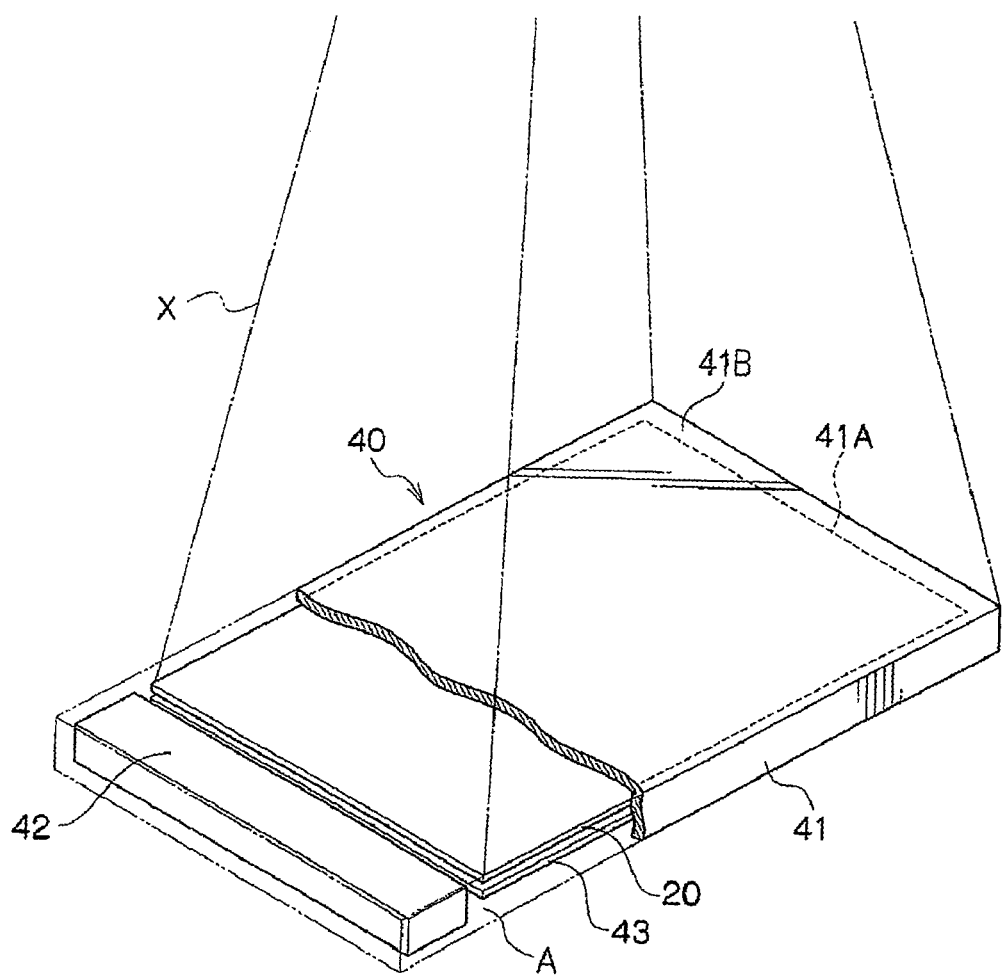
FIG. 5 is a perspective view showing the structure of an electronic cassette relating to the exemplary embodiment.

The structure of the electronic cassette relating to the present exemplary embodiment is described next. FIG. 5 is a perspective view showing the structure of the electronic cassette 40 relating to the present exemplary embodiment. As shown in FIG. 5, the electronic cassette 40 has a housing 41 formed from a material through which radiation is transmitted, and is a structure that is waterproof and airtight. When the electronic cassette 40 is being used in an operating room or the like, there is the concern that blood or other various germs will stick thereto. Thus, by making the electronic cassette 40 be a waterproof and airtight structure and disinfectingly cleaning it as needed, the one electronic cassette 40 can be used repeatedly in continuation.

A space A that accommodates various parts is formed at the interior of the housing 41. The radiation detector 20 that detects the radiation X that has passed through the object of imaging, and a lead plate 43 that absorbs the back-scattered radiation of the radiation X, are disposed within the space A in that order from the irradiated surface side of the housing 41 onto which the radiation X is irradiated.

Here, at the electronic cassette 40, the region, that corresponds to the position where the radiation detector 20 is disposed, of one flat-plate-shaped surface of the housing 41 is made to be an imaging region 41A that is quadrilateral and that can detect radiation. This surface, that has the imaging region 41A, of the housing 41 is a ceiling plate 41B at the electronic cassette 40. In the electronic cassette 40 relating to the present exemplary embodiment, the radiation detector 20 is disposed such that the TFT substrate 30 becomes the ceiling plate 41B side, and is affixed to the surface, at the inner side of the housing 41, of this ceiling plate 41B (the surface, of the ceiling plate 41B, that is at the side opposite the surface thereof onto which radiation is irradiated).

On the other hand, a case 42, that accommodates a cassette controller 58 and a power source unit 70 (see FIG. 6) that are described later, is disposed at a position that does not overlap the radiation detector 20 (outside of the range of the imaging region 41A) at one end side of the interior of the housing 41. In order to lighten the weight of the electronic cassette 40 overall, the housing 41 is structured from, for example, carbon fibers, aluminum, magnesium, bio-nanofibers (cellulose microfibrils), or composite materials or the like.

For example, materials containing a fiber-reinforced resin are used as the composite material, and carbon, cellulose and the like are included in fiber-reinforced resins. Concretely, carbon fiber-reinforced plastic (CFRP), materials of a structure in which a foamed material is sandwiched by CFRP, materials in which CFRP is coated on the surface of a foamed material, or the like are used as the composite material. Note that, in the present exemplary embodiment, a material of a structure in which a foamed material is sandwiched by CFRP is used. Due thereto, the strength (rigidity) of the housing 41 can be increased as compared with a case in which the housing 41 is structured by carbon alone.

Figure 6:
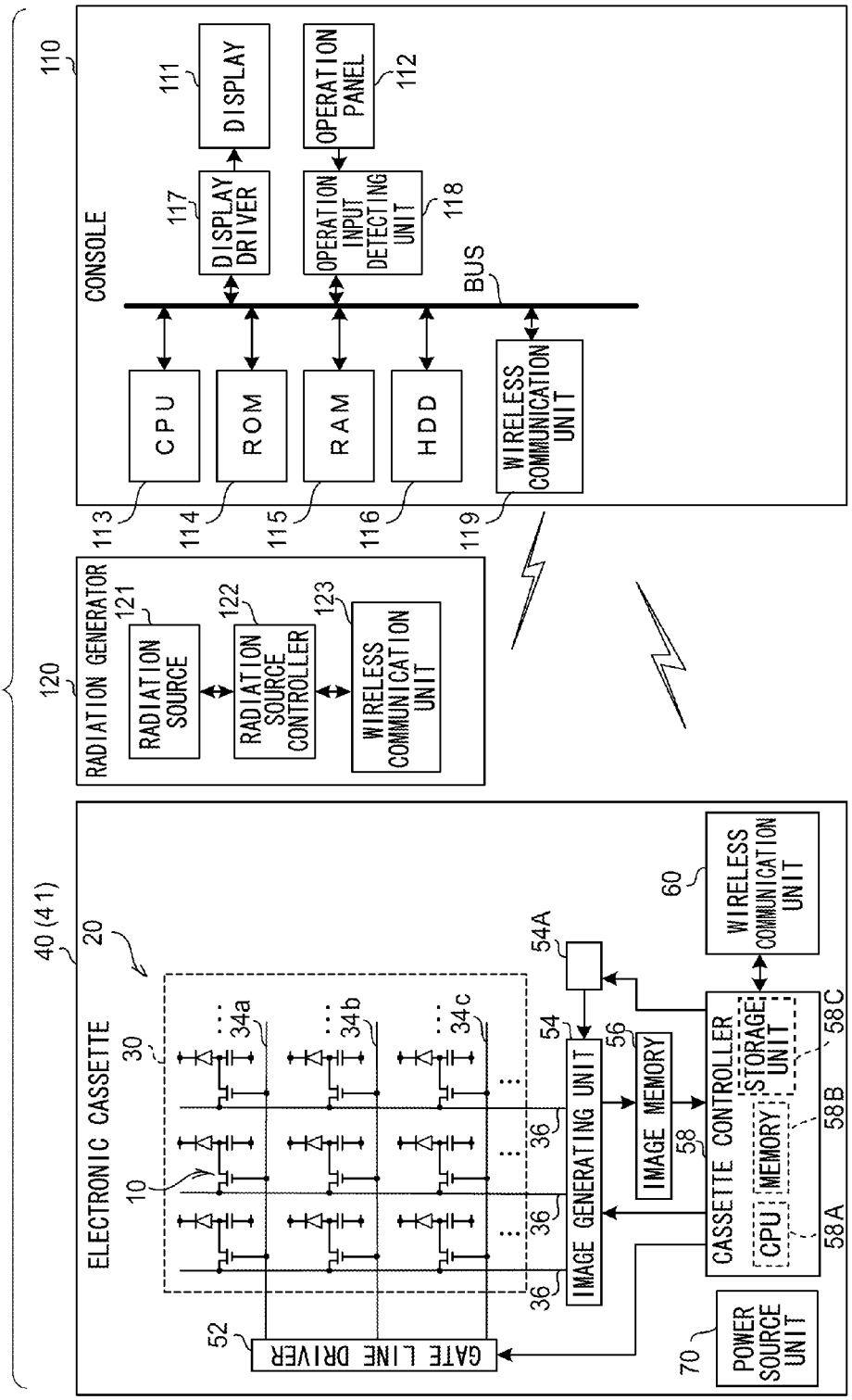
FIG. 6 is a block diagram showing the structure of the radiographic image capturing system relating to the exemplary embodiment.

The structures of main portions of the electrical system of the radiographic image capturing system relating to the present exemplary embodiment are explained next. FIG. 6 is a block diagram showing the structure of the radiographic image capturing system, and including the structures of the main portions of the electrical system of the electronic cassette 40. In FIG. 6, a gate line driver 52 is disposed at one side among two adjacent sides of the radiation detector 20 that is built-into the electronic cassette 40, and an image generating unit 54 is disposed at the other side. The individual gate lines 34 (shown individually as gate lines 34a, 34b, . . . in FIG. 6, and these reference numerals are used as needed) of the TFT substrate 30 are connected to the gate line driver 52, and the individual data lines 36 of the TFT substrate 30 are connected to the image generating unit 54. Further, an image memory 56, the cassette controller 58 and a wireless communication unit 60 are provided within the housing 41.

The respective thin film transistors 10 of the TFT substrate 30 are turned on in order and row-by-row by signals supplied from the gate line driver 52 via the gate lines 34. The charges, that are read-out by the thin film transistors 10 that have been turned on, are transferred as electric signals through the data lines 36 and are inputted to the image generating unit 54. Due thereto, charges are read-out in order in units of rows, and a two-dimensional radiographic image can be acquired.

Figure 7:
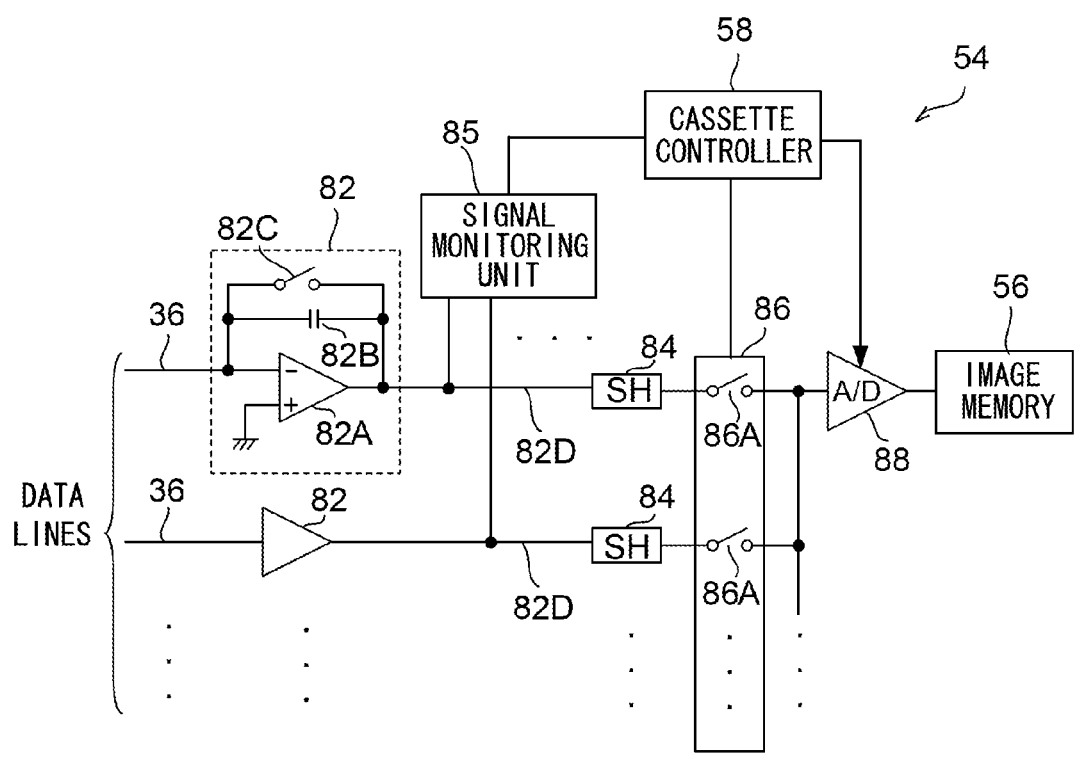
FIG. 7 is a circuit diagram showing the structure of an image generating unit relating to the exemplary embodiment.

Next, the structure of the image generating unit 54 relating to the present exemplary embodiment is described. FIG. 7 is a circuit diagram showing the structure of the image generating unit 54 relating to the present exemplary embodiment. As shown in FIG. 7, the image generating unit 54 has, in correspondence with each of the data lines 36, a variable gain pre-amplifier (charge amplifier) 82 and a sample-and-hold circuit 84. The variable gain pre-amplifier 82 is structured to include an operational amplifier 82A whose positive input (non-inverting terminal) side is grounded, and a capacitor 82B and a reset switch 82C that are respectively connected in parallel between the negative input (inverting terminal) side and the output side of the operational amplifier 82A. The reset switch 82C is switched by the cassette controller 58.

Further, the image generating unit 54 has a signal monitoring unit 85 that monitors the respective output waveforms of the variable gain pre-amplifiers 82, the sample-and-hold circuits 84 that sample and hold the outputs of the variable gain pre-amplifiers (charge amplifiers) 82, a multiplexer 86, and an A/D (analog/digital) converter 88. Note that the sampling timing of the sample-and-hold circuits 84, and also the output selected by switches 86A provided at the multiplexer 86, are switched by the cassette controller 58.

At the time of detecting a radiographic image, first, due to the cassette controller 58 turning the respective reset switches 82C of the variable gain pre-amplifiers 82 on for a predetermined time period, the charges accumulated in the respective capacitors 82 are discharged. On the other hand, the charges, that are accumulated in the respective capacitors 9 of the pixels 32 that acquire a radiographic image due to the radiation X being irradiated, are, due to the connected thin film transistors 10 being turned on, transferred as electric signals through the connected data lines 36. The electric signals that are transferred through the data lines 36 are amplified at a predetermined amplification factor by the corresponding variable gain pre-amplifiers 82.

After carrying out the above-described discharging, due the cassette controller 58 driving the sample-and-hold circuits 84 for a predetermined time period, the signal levels of the electric signals amplified by the variable gain pre-amplifiers 82 are held in the sample-and-hold circuits 84. Then, the signal levels held in the respective sample-and-hold circuits 84 are selected in order by the multiplexer 86 in accordance with control by the cassette controller 58, and are A/D-converted by the A/D converter 88. Image data expressing the captured radiographic image is thereby generated.

Note that an image generating unit power source 54A, that supplies electric power for driving to the image generating unit 54, is provided at the electronic cassette 40 relating to the present exemplary embodiment. The image generating unit power source 54A relating to the present exemplary embodiment is structured by a DC-DC converter whose power input end is connected to the power source unit 70 that is described later. The output end of this DC-DC converter is connected to the variable gain pre-amplifiers 82, the sample-and-hold circuits 84, the multiplexer 86, and the A/D converter 88 of the image generating unit 54.

As shown in FIG. 6, the cassette controller 58 is connected to the control input end of the image generating unit power source 54A. The start of the supplying of electric power and the stoppage of the supplying of electric power from the image generating unit power source 54A is controlled by the cassette controller 58. On the other hand, the image memory 56 is connected to the image generating unit 54, and the image data, that is outputted from the A/D converter 88 of the image generating unit 54, is stored in order in the image memory 56. The image memory 56 has a storage capacity that can store image data of several images. Each time capturing of a radiographic image is carried out, the image data obtained by the capturing is successively stored in the image memory 56.

The image memory 56 is connected to the cassette controller 58. The cassette controller 58 is structured to include a microcomputer, and has a CPU (Central Processing Unit) 58A, a memory 58B including a ROM (Read Only Memory) and a RAM (Random Access Memory), and a non-volatile storage unit 58C formed from a flash memory or the like. The cassette controller 58 controls the overall operations of the electronic cassette 40.

Note that the wireless communication unit 60 is connected to the cassette controller 58. The wireless communication unit 60 corresponds to wireless LAN (Local Area Network) standards such as IEEE (Institute of Electrical and Electronics Engineers) 802.11a/b/g/n or the like, and controls the transfer of various types of data to and from external devices by wireless communication. Via the wireless communication unit 60, the cassette controller 58 can communicate wirelessly with external devices such as the console and the like, that carry out control relating to the capturing of radiographic images, and the transmission and reception of various types of data to and from the console and the like is possible.

A power source unit 70 is provided at the electronic cassette 40. The above-described various types of circuits and respective elements (the gate line driver 52, the image generating unit 54, the image memory 56, the wireless communication unit 60, the microcomputer that functions as the cassette controller 58, and the like) are operated by electric power supplied from the power source unit 70. The power source unit 70 incorporates therein a battery (a rechargeable secondary battery) so that the portability of the electronic cassette 40 is not impaired, and supplies electric power from the charged battery to the various types of circuits/elements. Note that, in FIG. 6, the wires that connect the power source unit 70 with the various types of circuits and respective elements are omitted.

On the other hand, as shown in FIG. 6, the console 110 is structured as a server computer, and has a display 111 that displays an operation menu, captured radiographic images and the like, and an operation panel 112 that is structured to include plural keys and at which various types of data and operating instructions are inputted.

The console 110 relating to the present exemplary embodiment has a CPU 113 that governs the operations of the overall device, a ROM 114 in which various types of programs, including control programs, and the like are stored in advance, a RAM 115 that temporarily stores various types of data, an HDD (Hard Disk Drive) 116 that stores and holds various types of data, a display driver 117 that controls the display of various types of data on the display 111, and an operation input detecting unit 118 that detects the operated state of the operation panel 112. Further, the console 110 has a wireless communication unit 119 that, by wireless communication, carries out transmission and reception of various types of data, such as exposure conditions that will be described later and the like, to and from the radiation generator 120, and carries out transmission and reception of various types of data, such as image data and the like, to and from the electronic cassette 40.

The CPU 113, the ROM 114, the RAM 115, the HDD 116, the display driver 117, the operation input detecting unit 118, and the wireless communication unit 119 are connected to one another via a system bus BUS. Accordingly, the CPU 113 can access the ROM 114, the RAM 115 and the HDD 116, and can respectively carry out control of display of various types of data on the display 111 via the display driver 117, and control of transmission and reception of various types of data with the radiation generator 120 and the electronic cassette 120 via the wireless communication unit 119. Further, the CPU 113 can, via the operation input detecting unit 118, grasp the operated state of the operation panel 112 by a user.

On the other hand, the radiation generator 120 has a radiation source 121, a wireless communication unit 123 that transmits and receives various types of data, such as exposure conditions and the like, to and from the console 110, and a radiation source controller 122 that controls the radiation source 121 on the basis of received exposure conditions.

The radiation source controller 122 also is structured to include a microcomputer, and stores received exposure conditions and the like. Data such as the tube voltage, the tube current and the like is included in the exposure conditions received from the console 110. The radiation source controller 122 causes the radiation X to be irradiated from the radiation source 121 on the basis of the received exposure conditions.

Figure 8:
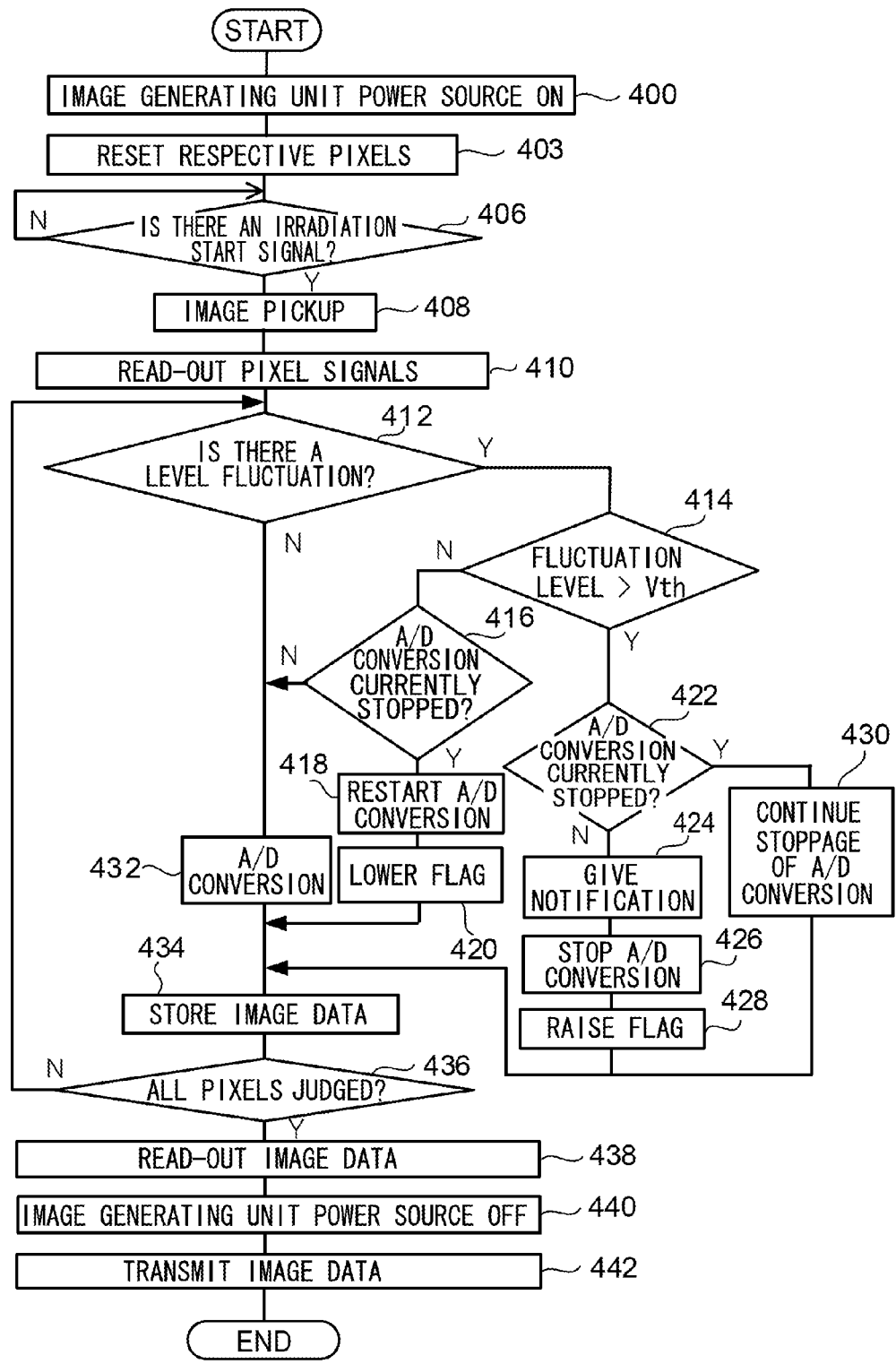
FIG. 8 is a flowchart showing the order of processings at the electronic cassette of the radiographic image capturing system relating to the exemplary embodiment.

Operation of the electronic cassette of the radiographic image capturing system relating to the present exemplary embodiment is described next. FIG. 8 is a flowchart showing the order of processings at the electronic cassette of the radiographic image capturing system. Note that FIG. 8 is a flowchart showing the flow of processings of a cassette imaging processing program that is executed by the CPU 58A at the cassette controller 58 of the electronic cassette 40, and this program is stored in advance in a predetermined area of the memory 58B.

In step 400 of FIG. 8, the image generating unit power source 54A is controlled so as to start the supply of electric power from the image generating unit power source 54A to the image generating unit 54. In next step 403, the gate line driver 52 is controlled so as to output on signals successively and line-by-line to the respective gate lines 34a, 34b, 34c, . . . from the gate line driver 52, and, by discharging the charges accumulated in the capacitors 9 at the respective pixels 32 of the radiation detector 20, the pixels 32 that are to acquire a radiographic image are reset. Note that the resetting operation of the respective pixels 32 that is carried out by the processing of step 403 may be repeated plural times.

In next step 406, the cassette controller 58 of the electronic cassette 40 judges, for example, whether or not there is an instruction signal, that instructs the start of exposure of the radiation X, from the console 110. When this instruction signal is received, in step 408, the cassette controller 58 starts the accumulation of charges in the capacitors 9 at the respective pixels 32 of the radiation detector 20, and thereby starts the radiographic image capturing operation. Then, the cassette controller 58 ends the radiographic image capturing operation on the basis of, for example, a radiation dose cumulative value (threshold value) that is based on predetermined radiation dose data.

In next step 410, pixel signals (charge signals) are read-out. Namely, the gate line driver 52 is controlled such that on signals are outputted in order and line-by-line from the gate line driver 52 to the respective gate lines 34a, 34b, 34c, . . . , and the respective thin film transistors 10 that are connected to the respective gate lines 34 are turned on in order and line-by-line. When the respective thin film transistors 10, that are connected to the respective gate lines 34a, 34b, 34c, . . . of the radiation detector 20 are turned on in order and line-by-line, the charges accumulated in the respective capacitors 9 flow-out, in order and line-by-line, to the respective data lines 36 as electric signals. The electric signals that have flowed-out to the respective data lines 36 are inputted to the variable gain pre-amplifiers (charge amplifiers) 82 that are disposed in respective correspondence therewith.

Figure 9:
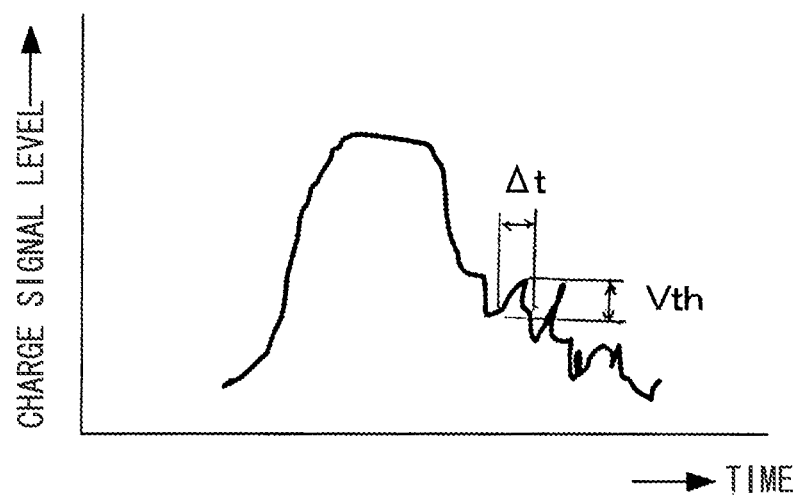
FIG. 9 is a drawing for explaining a level fluctuation of an output waveform from a variable gain preamplifier.

In step 412, the output waveforms from the respective variable gain pre-amplifiers 82 are monitored by the signal monitoring unit 85 that is connected to output lines 82D of the respective variable gain pre-amplifiers 82. FIG. 9 is an example of the charge signal waveform at one pixel that has been amplified at the variable gain pre-amplifier 82. FIG. 9 shows a state in which, as a result of the charge signal being affected by noise or the like, level fluctuations arise in portions of the signal output waveform from the gain pre-amplifier 82.

The level fluctuations of the output waveform here are thought to be due to the effects of electromagnetic wave noise or the like that reaches the radiation detector 20 of the electronic cassette 40 that handles minute signals. More concretely, in the driving system of a so-called modality system overall, there is internal noise such as, for example, noise that is generated at the interior of the electronic cassette, motor driving noise, noise that accompanies the driving of a compression plate in the case of mammography, noise that depends on the communication system, and the like. Further, as external noise, there is, for example, noise that derives from electrocautery during surgery or the like. In addition, in a case in which mechanical vibrations are applied to the electronic cassette, dummy noise, that is due to vibrations of flexible substrates that are used in connection between substrates, and the like, at the electronic cassette interior, also arises.

In above-described step 412, if, as a result of monitoring the output waveforms from the respective variable gain pre-amplifiers 82 by the signal monitoring unit 85, there is a level fluctuation in the amplifier-outputted waveform of a pixel signal, in step 414, the cassette controller 58 judges whether or not the level fluctuation has occurred within a predetermined minute time $\Delta t$ and is within a predetermined threshold value Vth. If it is judged in step 412 that there is no level fluctuation in the output waveform of the variable gain pre-amplifier 82, the processing moves on to step 432, and A/D conversion is carried out on that pixel signal.

On the other hand, if it is judged in step 414 that the level fluctuation within the minute time $\Delta t$ of the output waveform from the variable gain pre-amplifier 82 exceeds the predetermined threshold value Vth, in step 422, it is judged whether or not the A/D conversion by the A/D converter 88 is currently stopped. If the A/D conversion is not currently stopped, in step 424, the fact that the output level fluctuation has exceeded the threshold value is notified to the technician or the like by, for example, being visually displayed on the display portion of the console 110, or by an audible sound being emitted from a speaker or the like. Then, in step 426, the cassette controller 58 transmits an operation stop signal to the A/D converter 88 so that A/D conversion will not be carried out on the amplifier-outputted waveform of the charge signal of the pixel at which the level fluctuation exceeded the threshold value. In next step 428, a flag is raised at (a flag is added to) the captured image data, as data identifying that the threshold value has been exceeded. Due thereto, the point in time (timing) at which the aforementioned threshold value was exceeded in the time period of the capturing of the radiographic image is made clear. Thereafter, the processing moves on to step S434.

Note that, if it is judged in step 422 that the A/D conversion is currently stopped, in step 430, the stoppage of the A/D conversion by the A/D converter 88 is continued, and thereafter, the processing moves on to step S434. Further, notification when a level fluctuation is sensed may be given each time a level fluctuation is sensed, or may be given a single time.

Even if a level fluctuation is detected in step 412, if it is judged in step 414 that that level fluctuation is within the threshold value Vth, the processing moves on to step 416 and it is judged whether or not the A/D conversion by the A/D converter 88 is currently stopped. If the A/D conversion is not currently stopped, processing moves on to step 432 and A/D conversion is carried out on that pixel signal. On the other hand, if it is judged in step 416 that A/D conversion is currently stopped, in step 418, it is judged that the level fluctuation of the charge signal output for that pixel has converged. Then, operation of the A/D converter 88 that was stopped in above step 426 is re-started, and, in next step 420, the flag that was raised in above step 428 is lowered.

In step 432, selection of a signal by the switches 86A provided at the multiplexer 86 is carried out with respect to the analog output signals that have passed through the sample-and-hold circuits 84, and the selected analog output signals are successively converted into digital image data by the A/D converter 88. Then, in step 434, the data after the A/D conversion is stored in the image memory 56.

In step 436, it is judged whether or not the judgment as to the existence of a level fluctuation in the amplifier-outputted waveform from the variable gain pre-amplifier 82 has been made with respect to the pixel signals (charge signals) of all of the pixels that were read-out in step S410. If the judgment regarding a level fluctuation has not been carried out for all of the pixels, processing returns to step 412, and a level fluctuation within the minute time $\Delta t$ of the amplifier-outputted waveform is detected for the next pixel by the signal monitoring unit 85 in the same way as described above. However, if it is judged in step S436 that the absence/presence of a level fluctuation of the pixel signal has been sensed for all of the pixels, processing moves on to step 438.

In step 438, the image data, that was stored in the image memory 56 in above-described step 434, is read-out. In next step 440, the respective pixels 32 for radiographic image acquisition are reset by discharging the charges at which dark current has accumulated and the remaining charges after completion of reading-out of the charges of the capacitors 9 at the respective pixels 32 of the radiation detector 20. Then, the image generating unit power source 54A is controlled so as to stop the supply of electric power from the image generating unit power source 54A to the image generating unit 54. In next step 442, the read-out image data is transmitted to the console 110 via the wireless communication unit 60, and the present cassette imaging processing program ends.

Note that, here, when detecting level fluctuations in the amplifier-outputted waveforms, the electric signals of the pixels 32 disposed at the radiation detector 20 may be made to be the objects of monitoring of level fluctuations, or some of the pixels of the radiation detector 20 may be made to be synchronization-free pixels and the charge signals of these synchronization-free pixels may be made to be the objects of monitoring of level fluctuations. Or, a sensor that is different from the pixels may be provided separately, and may detect level fluctuations of the amplifier-outputted waveforms. Further, instead of monitoring level fluctuations of the amplifier-outputted waveforms, the level fluctuations (deviation) of dark noise (white noise) may be monitored at times of standby after the exposure of the radiation X. Moreover, in monitoring level fluctuations of the amplifier-outputted waveforms, level fluctuations of the captured signals may be monitored at the time of capturing the radiographic image, and level fluctuations of dark noise (white noise) may be monitored at times of standby after the exposure of the radiation X. Due thereto, at times of standby as well, the absence/presence of driving of noise sources is sensed, and appropriate judgments and measures based thereon can be made.

In the present exemplary embodiment, the stopping of the A/D conversion operation at the A/D converter 88 when the level fluctuation of the amplifier-outputted waveform is judged to exceed the predetermined threshold value Vth may be carried out by, for example, the cassette controller 58 writing a predetermined value (reset data) to the AD control register of the A/D converter 88 and stopping operation, or the supply of electric power to the A/D converter 88 may be cut-off by an unillustrated switch or the like. Further, the A/D conversion operation may be restarted by inputting predetermined data to the AD control register of the A/D converter 88 and starting operation, or the A/D conversion operation may be restarted by the supply of electric power due to turning-on of the aforementioned switch.

Note that, when the radiation detector 20 is a so-called reverse reading-type in which radiation is irradiated from the side at which the scintillator 8 shown in FIG. 2 is formed and the radiographic image is read from the TFT substrate 30 that is provided at the obverse surface side of the incident surface of the radiation, light is emitted more strongly at the top surface side of the scintillator 8 (the side opposite the TFT substrate 30). When the radiation detector 20 is a so-called obverse reading-type (ISS: Irradiation Side Sampling) in which radiation is irradiated from the TFT substrate 30 side and the radiographic image is read from the TFT substrate 30 that is provided at the obverse side of the incident surface of the radiation, the radiation transmitted through the TFT substrate 30 is incident on the scintillator 8, and the TFT substrate 30 side of the scintillator 8 emits light more strongly. At the respective sensor portions 13 provided at the TFT substrate 30, charges are generated due to the light generated at the scintillator 8. Therefore, when the radiation detector 20 is an obverse reading-type, the light emitting position of the scintillator 8 with respect to the TFT substrate 30 is closer and therefore the resolution of the radiographic image obtained by imaging is higher, than when the radiation detector 20 is a reverse reading-type (PSS: Penetration Side Sampling).

Further, at the radiation detector 20, the photoelectric conversion film 4 is structured of an organic photoelectric conversion material, and hardly any radiation is absorbed at all at the photoelectric conversion film 4. Therefore, at the radiation detector 20 relating to the present exemplary embodiment, even when radiation passes through the TFT substrate 30 in accordance with the obverse reading-type radiation detector, the amount of radiation absorbed by the photoelectric conversion film 4 is low, and therefore, a decrease in sensitivity with respect to radiation can be suppressed. In an obverse reading-type radiation detector, radiation passes through the TFT substrate 30 and reaches the scintillator 8. However, when the photoelectric conversion film 4 of the TFT substrate 30 is structured of an organic photoelectric conversion material in this way, there is hardly any absorption of radiation at the photoelectric conversion film 4, and damping of radiation can be kept low. Therefore, the photoelectric conversion film 4 that is structured of an organic photoelectric conversion material is suited to an obverse reading-type radiation detector.

Further, with all of the amorphous oxides that structure the active layer 17 of the thin film transistor 10 and the organic photoelectric conversion materials that structure the photoelectric conversion film 4, film formation at a low temperature is possible. Therefore, the substrate 1 can be formed of a plastic resin, aramid, or bio-nanofibers that have low absorption of radiation. Because the absorbed amount of radiation is low at the substrate 1 that is formed in this way, even when radiation passes through the TFT substrate 30 in accordance with an obverse reading-type radiation detector, a deterioration in sensitivity with respect to radiation can be suppressed.

As described above in detail, in the present exemplary embodiment, the actual output waveform from the variable gain pre-amplifier is monitored, and, when a level fluctuation in the output waveform exceeds a predetermined threshold value, A/D conversion operation of the output signal by the A/D converter is stopped. Thereafter, if the level fluctuation is within the predetermined threshold value, it is judged that the level fluctuation has subsided, and control is carried out so as to restart operation of the A/D converter. Due thereto, in the stage before the amp output signal is A/D-converted, a level fluctuation in the image signal due to mixing-in of noise or the like is sensed, and it can be known in advance that a deterioration in quality of the captured image has arisen.

As a result, wasteful operation stoppage time does not arise in the image pickup work or the image pickup processing, and in addition, deterioration in image quality due to mixing-in of noise or the like can be known in advance. Therefore, there is the marked effect that diagnosis, that is carried out by a doctor or the like by using the captured image, is not affected. In particular, electronic cassettes, that are easily affected by noise caused by external disturbances such as impact or electromagnetic waves or the like, can be structured so as to deal with deterioration in image quality due to level fluctuations in analog image signals.

Further, in the present exemplary embodiment, the absence/presence of level fluctuations in the image signals is not judged by analyzing the radiographic image after capturing, and the absence/presence of level fluctuations, and the extents of the level fluctuations, are judged by directly monitoring the output waveforms from the variable gain pre-amplifiers. Therefore, image deterioration that accompanies monitoring and judging of level fluctuations does not arise.

Moreover, control is carried out to add a flag to the image data at the time when a level fluctuation in the output waveform is detected, and to lower the flag together with the converging of the level fluctuation. Due thereto, it is easy to achieve correspondence between the time period from the raising of the flag to the lowering of the flag, and the time period from the arising of the fluctuation in the signal level to the converging of the signal level fluctuation during the time period of capturing the radiographic image. As a result, the image portions that are affected by level fluctuations due to noise or the like are discriminated easily and can be tracked down. Therefore, mis-diagnosis during the diagnosing, that is carried out by a doctor or the like and by using the captured image, can effectively be prevented.

The present invention has been described above by using an exemplary embodiment, but the technical scope of the present invention is not limited to the scope described in the above exemplary embodiment. Various changes or improvements can be added to the above-described exemplary embodiment within a scope that does not deviate from the gist of the invention, and forms to which such changes or modifications are added also are included in the technical scope of the present invention.

Further, the above exemplary embodiment does not limit the inventions relating to the claims, and it is not necessarily the case that all of the combinations of features described in the exemplary embodiment are essential to the means of the present invention for solving the problems of the prior art. Inventions of various stages are included in the above exemplary embodiment, and various inventions can be extracted by appropriately combining plural constituent features that are disclosed. Even if some of the constituent features are removed from all of the constituent features that are illustrated in the exemplary embodiment, such structures from which some constituent features are removed can be extracted as inventions provided that the effects of the present invention are obtained thereby.

For example, in the above-described exemplary embodiment, when the level fluctuation of the output waveform of a variable gain pre-amplifier exceeds the threshold value, the operation of the A/D converter is stopped, and thereafter, when the level fluctuation has subsided to within the threshold value, operation of the A/D converter is restarted. However, the present invention is not limited to the same. For example, because operation times at the driving system of the radiographic image capturing system can be predicted in advance, there may be a structure in which a timer is activated at the time when a level fluctuation of the output waveform of a variable gain pre-amplifier exceeds the threshold value, and, after a given time elapses, operation is automatically restored so as to restart the operation of the A/D converter.

Moreover, a region of interest (ROI), that is a portion that the doctor focuses on, may be designated in advance in a radiographic image, and the threshold value for judging the level fluctuation of the output waveform of the variable gain pre-amplifier may be changed in accordance with whether the corresponding pixel is within the region of interest or outside of the region of interest. FIG. 10 is a flowchart showing processing of changing the threshold value for the level fluctuation judgment in accordance with whether the corresponding pixel is within the region of interest or outside of the region of interest. Processings that are the same as processings shown in FIG. 8 are denoted by the same reference numerals, and description thereof is omitted here.

For example, in step 401 of FIG. 10, the position of the region of interest, that corresponds to the region to be imaged of the subject, on the radiation irradiating surface of the radiation detector 20 is set. Concretely, positional data, that expresses the position of a standard region of interest of the region to be imaged of the subject, is inputted. Further, the threshold value for level fluctuation judgment within the region of interest is set to Vth1, and the threshold value for level fluctuation judgment outside of the region of interest is set to Vth2. Then, in step 412, if, as a result of monitoring the output waveforms from the respective variable gain pre-amplifiers 82, there is a level fluctuation in an amplifier-outputted waveform of a pixel signal, the routine moves on to step 452. In step 452, it is judged whether the pixel of the read-out charge signal is a pixel that is within the region of the set region of interest, or is a pixel that is outside of this region. Then, the threshold values for level fluctuation judgment, that differ in accordance with whether the corresponding pixel is within the region of interest or outside of the region of interest, are used on the basis of the results of this judgment.

More concretely, if the pixel in question is a pixel that is within the region of the region of interest, in step 454, Vth1 is used as the level fluctuation judgment threshold value for within the region of interest, and it is judged whether or not the level fluctuation of the output waveform of the variable gain pre-amplifier 82 is within the range of Vth1. On the other hand, if the pixel in question is a pixel that is outside of the region of the region of interest, in step 456, Vth2 is used as the level fluctuation judgment threshold value for outside of the region of interest, and it is judged whether or not the level fluctuation of the amplifier-outputted waveform is within the range of Vth2.

Note that, here, by setting the threshold value Vth1 for within the region of interest to be smaller (more severe) than the threshold value Vth2 for outside of the region of interest, even in cases in which there is a relatively small level fluctuation, at an image region that is set as the region of interest, image quality deterioration due to level fluctuations in the amplifier-outputted waveforms can be effectively removed from the captured image, and, in the diagnosing process, instances of mis-diagnosis with respect to important regions can be reduced. Further, when a level fluctuation of an amplifier-outputted waveform is detected, reading-out of the pixel signals of within the region of interest may be stopped, and thereafter, after a predetermined time elapses, reading-out of the pixel signals of within the region of interest may be carried out, and the analog signals, that are obtained by the acquired charge signals being amplified at the variable gain pre-amplifiers, may be A/D-converted. The image of an important region to be diagnosed can be obtained at a higher image quality by, within the region of interest and separately from outside of the region of interest, carrying out reading-out of the pixel signals at a point in time when the effects of noise have disappeared and carrying out A/D conversion.

In the above-described exemplary embodiment, level fluctuations of a static image are handled, but the present invention is not limited to the same. For example, in the case of judging level fluctuations of video images, the threshold value of the level fluctuation judgment can be set to be more lax (smaller) than that for a static image. This is because, with video images, the captured images are provided in continuation, and therefore, it is thought that image diagnosis is not affected even if there is some deterioration in image quality due to mixing-in of noise. Note that, in the level fluctuation sensing of video images as well, when there is a level fluctuation that exceeds the threshold value, notification is given of that fact. By doing so, it can be left up to the technician who is handling the radiation to judge whether or not to continue with the capturing of the video images.

Moreover, at a radiographic image capturing system to which a radiation source of radiation is connected, when there is a level fluctuation that exceeds the threshold value in either of a still image or video images, the exposure of radiation from the radiation source may be stopped together with the notifying of the fact that there is such a level fluctuation. In this case, although not illustrated, a processing that stops exposure of radiation may be added after the processing of step 424 in FIG. 8 for example.

The above exemplary embodiment describes a case in which exposure conditions are set from the console 110, and when starting of exposure is instructed, exposure of radiation from the radiation source 121 is carried out by the radiation generator 120. However, the present invention is not limited to the same. For example, there may be a form in which a switch, that is operated by the person capturing the images or the like at times of starting exposure of the radiation and at times of ending the exposure, is provided at the radiation generator 120, and control is carried out by the radiation source controller of the radiation generator 120 so as to carry out starting and stopping of the exposure of radiation in accordance with the operation of this switch.

Further, although the above exemplary embodiment describes a case in which the radiation detecting elements of the present invention are provided at the TFT substrate 30, the present invention is not limited to the same. For example, the radiation detecting elements may be provided at a substrate, that is different than the TFT substrate 30, within the electronic cassette 40. Further, there may be a form in which the radiation detecting elements are provided as a body separate from the electronic cassette 40 so as to overlap the radiation incident side or the side opposite to this incident side, or the like. In these cases as well, effects that are similar to those of the above-described exemplary embodiment can be exhibited.

Moreover, the above exemplary embodiment describes a case in which the sensor portions 13 are structured so as to include an organic photoelectric conversion material that generates charges by receiving light generated at the scintillator 8. However, the present invention is not limited to the same, and may be a form that is applied to a structure in which the sensor portions 13 are structured without containing an organic photoelectric conversion material. Further, although a structure having the scintillator that converts irradiated radiation into visible light is described as the radiation detector that is incorporated in the electronic cassette, the present invention is not limited to the same. The radiation detector may be a direct-conversion-type radiation detector that uses a radiation-charge conversion material, such as amorphous selenium or the like, at a photoelectric conversion layer that absorbs radiation and converts the radiation into charges.

Still further, the above exemplary embodiment describes a case in which the radiation detector 20 and the case 42, that accommodates the cassette controller 58 and the power source unit 70, are disposed within the housing 41 of the electronic cassette 40 so as to not overlap, but the present invention is not limited to the same. For example, the radiation detector 20, and the cassette controller 58 and/or the power source unit 70, may be disposed so as to overlap.

The above exemplary embodiment describes a case in which communication between the electronic cassette 40 and the console 110, and communication between the radiation generator 120 and the console 110, are carried out wirelessly. However, the present invention is not limited to the same. For example, at least one of these communications may be made to be a form in which communication is carried out by using wires. Further, although description is given of a case in which X-rays are used as the radiation in the above exemplary embodiment, the present invention is not limited to the same, and may be a form that utilizes another type of radiation such as γ-rays or the like.

In addition, the structure of the electronic cassette 40 and the structure of the radiographic image capturing system 104 that are described in the above exemplary embodiment are examples, and, of course, unnecessary portions may be deleted therefrom, new portions may be added thereto, and the states of connection and the like may be changed within a scope that does not deviate from the gist of the present invention. Further, the structures of the data described in the above exemplary embodiment also are examples, and, of course, unnecessary data may be deleted or new data may be added within a scope that does not deviate from the gist of the present invention.

Further, the flows (see FIG. 8) of the processings of the various types of programs described in the above exemplary embodiment also are examples. Of course, unnecessary steps thereof may be deleted therefrom, new steps may be added thereto, or the order of the processings thereof may be rearranged within a scope that does not deviate from the gist of the present invention.

What is claimed is:

1. A radiographic image detection device comprising:
   an image pickup unit, that has a plurality of radiation detection portions that are arrayed in a two-dimensional form and that detect radiation, and that captures a radiographic image expressed by radiation that has been transmitted through an object of imaging and is incident on the image pickup unit;
   a radiographic image generating unit having a plurality of analog signal generating units that are provided in respective correspondence with the plurality of radiation detection portions and that each generate an analog signal corresponding to a radiation dose detected at the corresponding radiation detection portion;
   a conversion unit that converts the analog signals, that are generated respectively at the plurality of analog signal generating units, into digital signals;
   a judging unit that is configured to monitor a level fluctuation of the analog signal by directly monitoring a waveform of the analog signal over a predetermined minute time and judges whether or not the level fluctuation, over the predetermined minute time of the analog signal generated at each of the plurality of analog signal generating units is within a predetermined threshold value; and
   a control unit that controls the conversion unit such that an analog signal, at which it is judged by the judging unit that the level fluctuation is within the predetermined threshold value, is converted into a digital signal, and that controls the conversion unit such that an analog signal, at which it is judged that the level fluctuation has exceeded the predetermined threshold value, is not converted into a digital signal.

2. The radiographic image detection device of claim 1, wherein each of the plurality of analog signal generating units comprises an amplifier that generates an analog signal by amplifying a signal corresponding to a radiation dose detected at the radiation detection portion.

3. The radiographic image detection device of claim 1, wherein the control unit effects control so as to add identification data, that expresses a time when the level fluctuation of the analog signal exceeded the threshold value, to digital image data that is expressed by a digital signal obtained by conversion at the conversion unit, and so as to store the digital image data in a storage unit.

4. The radiographic image detection device of claim 2, wherein the control unit effects control so as to add identification data, that expresses a time when the level fluctuation of the analog signal exceeded the threshold value, to digital image data that is expressed by a digital signal obtained by conversion at the conversion unit, and so as to store the digital image data in a storage unit.

5. The radiographic image detection device of claim 1, wherein the judging unit judges whether or not a level fluctuation of the analog signal is within the predetermined threshold value, at at least one of:
   a time of pickup of the radiographic image, or
   a time of standby after irradiation of radiation.

6. The radiographic image detection device of claim 2 wherein the judging unit judges whether or not a level fluctuation of the analog signal is within the predetermined threshold value, at at least one of:
   a time of pickup of the radiographic image, or
   a time of standby after irradiation of radiation.

7. The radiographic image detection device of claim 3, wherein the judging unit judges whether or not a level fluctuation of the analog signal is within the predetermined threshold value, at at least one of:
   a time of pickup of the radiographic image, or
   a time of standby after irradiation of radiation.

8. The radiographic image detection device of claim 1, further comprising a notification unit that gives notice that the level fluctuation has exceeded the threshold value.

9. The radiographic image detection device of claim 5, further comprising a stopping unit that stops a radiation source of the radiation when notice is given by a notification unit.

10. The radiographic image detection device of claim 1, further comprising a region designation unit that designates in advance a region of interest in the radiographic image,
    wherein the threshold value is changed for the level fluctuation of the analog signal that expresses the radiographic image within the region of interest, and for a level fluctuation of an analog signal that expresses a radiographic image outside of the region of interest.

11. The radiographic image detection device of claim 2, further comprising a region designation unit that designates in advance a region of interest in the radiographic image,
    wherein the threshold value is changed for the level fluctuation of the analog signal that expresses the radiographic image within the region of interest, and for a level fluctuation of an analog signal that expresses a radiographic image outside of the region of interest.

12. The radiographic image detection device of claim 3, further comprising a region designation unit that designates in advance a region of interest in the radiographic image,
    wherein the threshold value is changed for the level fluctuation of the analog signal that expresses the radiographic image within the region of interest, and for a level fluctuation of an analog signal that expresses a radiographic image outside of the region of interest.

13. The radiographic image detection device of claim 5, further comprising a region designation unit that designates in advance a region of interest in the radiographic image,
    wherein the threshold value is changed for the level fluctuation of the analog signal that expresses the radiographic image within the region of interest, and for a level fluctuation of an analog signal that expresses a radiographic image outside of the region of interest.

14. The radiographic image detection device of claim 10, wherein, when the level fluctuation of the analog signal exceeds the threshold value, conversion by the conversion unit of an analog signal that expresses a radiographic image within the region of interest is carried out after a predetermined time elapses from a time when the level fluctuation exceeds the threshold value.

15. The radiographic image detection device of claim 11, wherein, when the level fluctuation of the analog signal exceeds the threshold value, conversion by the conversion unit of an analog signal that expresses a radiographic image within the region of interest is carried out after a predetermined time elapses from a time when the level fluctuation exceeds the threshold value.

16. The radiographic image detection device of claim 10, wherein, when the level fluctuation of the analog signal exceeds the threshold value, conversion by the conversion unit of an analog signal that expresses a radiographic image within the region of interest is carried out later than conversion by the conversion unit of an analog signal that expresses a radiographic image outside of the region of interest.

17. The radiographic image detection device of claim 1, wherein the image detection device is configured so that when the radiographic image is a video image, the judging unit judges whether or not the level fluctuation of the analog signal over the predetermined amount of time is within the threshold value that is smaller than when the radiographic image is a still image.

18. A radiographic image capturing system comprising:
    the radiographic image detection device of claim 1;
    a radiation generator; and
    a console that carries out transmission and reception of data with the radiographic image detection device and the radiation generator.

19. A radiographic image detection method comprising:
    capturing, by an image pickup unit that has a plurality of radiation detection portions that are arrayed in a two-dimensional form and detect radiation, a radiographic image expressed by radiation that has been transmitted through an object of imaging and is incident on the image pickup unit;
    generating, by each of a plurality of analog signal generating units that are provided in respective correspondence with the plurality of radiation detection portions, an analog signal that corresponds to a radiation dose detected at the corresponding radiation detection portion;
    judging whether or not a level fluctuation of the analog signal by directly monitoring a waveform of the analog signal over a predetermined minute time generated at each of the plurality of analog signal generating units is within a predetermined threshold value; and
    carrying out conversion into a digital signal on an analog signal, at which it is judged that the level fluctuation is within the predetermined threshold value, and stopping conversion into a digital signal of an analog signal, at which it is judged that the level fluctuation has exceeded the predetermined threshold value.

20. A non-transitory computer readable storage medium that stores a program for causing execution of processing by a radiographic image detection device that has: an image pickup unit that has a plurality of radiation detection portions that are arrayed in a two-dimensional form and detect radiation, and that captures a radiographic image expressed by radiation that has been transmitted through an object of imaging and been incident on the image pickup unit; a radiographic image generating unit having a plurality of analog signal generating units that are provided in respective correspondence with the plurality of radiation detection portions and that each generate an analog signal corresponding to a radiation dose detected at the corresponding radiation detection portion; and a conversion unit that converts the analog signals, that are generated respectively at the plurality of analog signal generating units, into digital signals, the processing comprising:

judging whether or not a level fluctuation of the analog signal generated by directly monitoring a waveform of the analog signal over a predetermined minute time at each of the plurality of analog signal generating units is within a predetermined threshold value; and controlling the conversion unit such that an analog signal, at which it is judged by the judging unit that the level fluctuation is within the predetermined threshold value, is converted into a digital signal, and controlling the conversion unit such that an analog signal, at which it is judged that the level fluctuation has exceeded the predetermined threshold value, is not converted into a digital signal.

* * * * *